(12) United States Patent
Kahlon

(10) Patent No.: US 12,714,827 B2
(45) Date of Patent: Aug. 25, 2026

(54) DUAL LUMEN HEMOSTATIC VALVE FOR GUIDING CATHETER

(71) Applicant: Arunpreet Kahlon, Highlands Ranch, CO (US)

(72) Inventor: Arunpreet Kahlon, Highlands Ranch, CO (US)

( * ) Notice: Subject to any disclaimer, the term of this patent is extended or adjusted under 35 U.S.C. 154(b) by 359 days.

(21) Appl. No.: 18/404,181

(22) Filed: Jan. 4, 2024

(65) Prior Publication Data

US 2024/0216645 A1 Jul. 4, 2024

Related U.S. Application Data

(60) Provisional application No. 63/478,435, filed on Jan. 4, 2023.

(51) Int. Cl.

*A61M 25/01* (2006.01)
*A61M 25/00* (2006.01)
*A61M 25/06* (2006.01)
*A61M 25/09* (2006.01)
*A61M 39/06* (2006.01)

(52) U.S. Cl.

CPC .... *A61M 25/0113* (2013.01); *A61M 25/0075* (2013.01); *A61M 25/0662* (2013.01); *A61M 25/09041* (2013.01); *A61M 39/06* (2013.01); *A61M 2025/0681* (2013.01)

(58) Field of Classification Search

CPC .................................................... A61M 39/06
See application file for complete search history.

(56) References Cited

U.S. PATENT DOCUMENTS 4,730,616 A * 3/1988 Frisbie .................. A61M 25/01 604/164.13
5,395,352 A * 3/1995 Penny ............... A61M 25/1025 604/533
5,935,112 A * 8/1999 Stevens ............ A61M 39/0613 604/246
6,270,477 B1 * 8/2001 Bagaoisan ........ A61M 25/0054 606/192
2003/0130577 A1 * 7/2003 Purdy .............. A61M 25/0662 604/523
2004/0172008 A1 * 9/2004 Layer ............... A61M 39/0613 604/533

(Continued)

OTHER PUBLICATIONS

"Options Matter", Merit Medical, [Online]. Retrieved from the Internet: <URL: https://www.merit.com/cardiac-intervention/intervention/hemostasis-valves-accessories/doubleplay-large-bore-hemostasis-valve/401010005>, (Dec. 31, 2022), 4 pgs.

*Primary Examiner* — David P. Olynick
(74) *Attorney, Agent, or Firm* — Schwegman Lundberg & Woessner, P.A.

(57) ABSTRACT

A multiple lumen hemostatic valve device can be used with a guide catheter in a medical intervention procedure. The valve device can include a manifold. A distal exit port can be coupled to the manifold and can provide a exit lumen. A first entry port can be coupled to the manifold and can provide a first entry lumen in communication with the exit lumen. A second entry port can be coupled to the manifold and can provide a second entry lumen in communication with the exit lumen. The first and second entry ports can be arranged to be parallel to each other and can respectively include independently operable first and second plunger valves.

16 Claims, 2 Drawing Sheets

(56) References Cited

U.S. PATENT DOCUMENTS

| | | | | |
|---|---|---|---|---|
| 2005/0245892 | A1 * | 11/2005 | Elkins | A61M 25/0043 604/264 |
| 2018/0184912 | A1 * | 7/2018 | Al-Ali | A61M 39/24 |
| 2018/0256872 | A1 * | 9/2018 | Agrawal | A61M 39/0613 |
| 2018/0256875 | A1 * | 9/2018 | Agrawal | A61M 39/06 |
| 2024/0216645 | A1 * | 7/2024 | Kahlon | A61M 25/09041 |
| 2024/0245895 | A1 * | 7/2024 | Oshimizu | A61M 39/06 |

* cited by examiner

DUAL LUMEN HEMOSTATIC VALVE FOR GUIDING CATHETER

CROSS-REFERENCE TO RELATED APPLICATION

This patent application claims the benefit of U.S. Provisional Patent Application No. 63/478,435, filed Jan. 4, 2024, which is incorporated by reference herein in its entirety.

TECHNICAL FIELD

This document pertains generally to medical instruments and methods of use and more particularly, but not by way of limitation, to a dual lumen hemostatic valve for guiding a catheter or other medical instrument, such as in a coronary intervention involving concurrent use of more than one guidewire, such as bifurcation percutaneous coronary interventions (PCI).

BACKGROUND

U.S. Patent Publication No. 2004/0172008A1 is directed toward a single lumen hemostasis valve.

U.S. Pat. No. 5,935,112 is also directed toward a single lumen hemostasis valve.

Merit Medical Systems, Inc. (South Jordan, Utah) has published online a product brochure that mentions a dual port hemostatis valve, referred to as DoublePlay™. (See https://www.merit.com/cardiac-intervention/intervention/hemostasis-valves-accessories/doubleplay-large-bore-hemostasis-valve/40101000S, visited Dec. 31, 2022). The divergent ports and threaded screw-in bore sealing of this device, however, make wire and instrument management difficult for the physician or other user.

SUMMARY/OVERVIEW

A hemostasis valve can include a valve body. The valve body can include a proximal end, such as for connecting to a first medical device and a distal end, such as for connecting to a second medical device. The hemostasis valve can include a first elongated chamber positioned within the valve body.

Hemostatic valves for guiding catheters can be used when performing coronary or other medical interventions. They allow entry of equipment into the blood vessels, such as through corresponding guide catheters, while maintaining hemostasis. The one-way valve at the back end allows entry of a guide wire, a balloon catheter, or a stent catheter, such as by pushing the cap. As the cap is released, the valve closes, which prevents back-bleeding.

Most hemostatic valves are single-lumen devices. With the ever increasing complexity of coronary interventions, more interventional medical procedures can benefit from concurrent or simultaneous use of two or more guide wires and/or two or more balloon and stent-delivery catheters. Performing certain procedures through a single lumen hemostatic valve can be difficult. Challenges of simultaneously using multiple guide wires and balloon and stent catheters can include sterile field management, entanglement, and accidental withdrawal, which can lead to complications.

Thus, the present inventor has recognized, among other things, that there is a need for a convenient and easy-to-use dual lumen hemostatic valve that can allow better management of multiple guide wires when used concurrently or simultaneously. The wire not being actively used can be held securely by the dual lumen hemostatic valve, thus helping to reduce or minimize occurrences of entanglement or accidental withdrawal. The present document describes, among other things, a dual lumen hemostatic valve that can avoid complications associated with divergent ports and threaded screw-in bore sealing.

This document describes, among other things, a dual lumen hemostatic valve that can be used for guiding a catheter used in coronary or other medical interventions that can benefit from concurrent or simultaneous use of more than one guide wire, such as a bifurcation percutaneous coronary intervention (PCI). For example, a hemostatic valve for guiding a catheter can include two exit lumens, such as which can respectively include separate corresponding hemostatic valves. This can help allow better management of multiple coronary guide wires and coronary devices.

For example, the present dual lumen hemostasis valve device can include a dual lumen pushable hemostatic valve for use in delivering a guide catheter used in coronary interventions. The back end of both lumens can include independently pushable valves that can be actuated independent of each other. This device is suitable for use in coronary interventions that involve concurrent or simultaneous use of more than one guide wire, such as bifurcation PCI.

This Summary/Overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
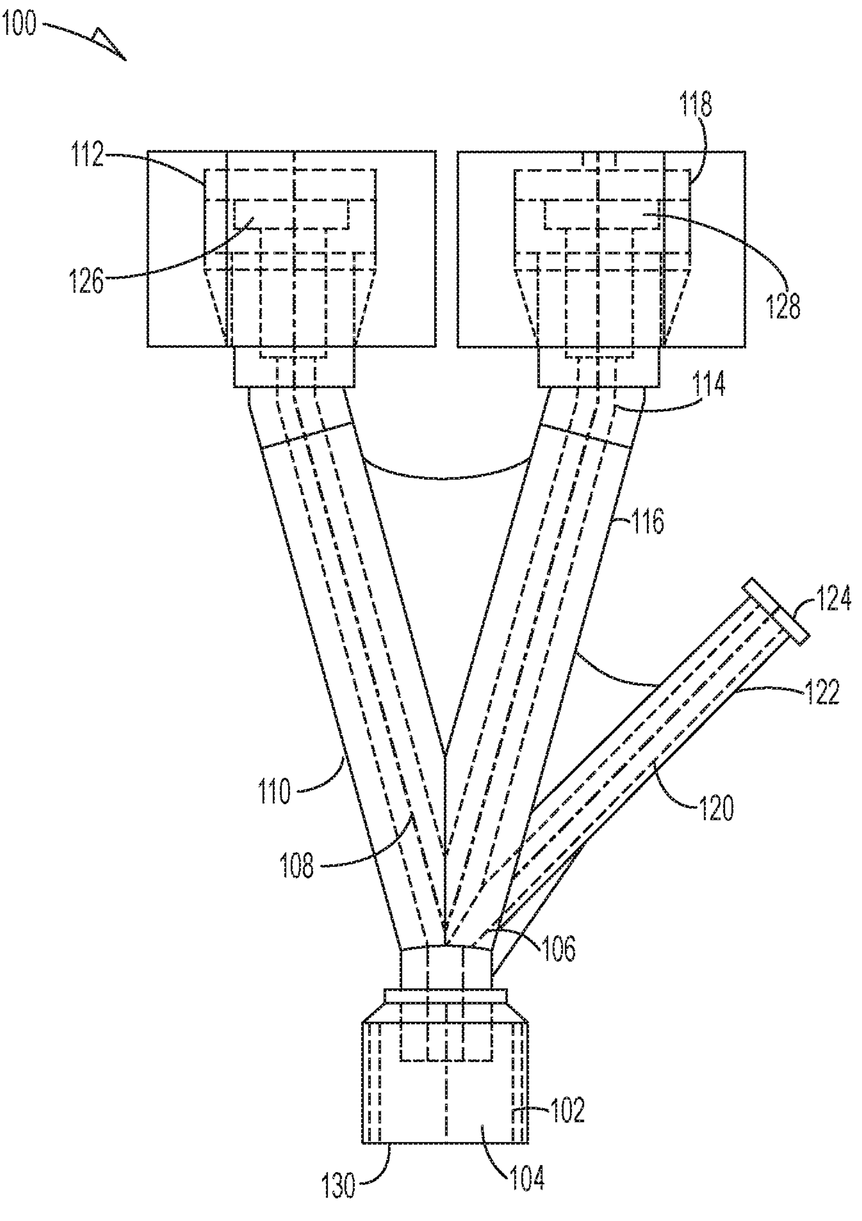
FIG. 1 shows an example of portions of a multiple (e.g., dual) lumen hemostatic valve device.

FIG. 1 shows an example of portions of a multiple (e.g., dual) lumen hemostatic valve device 100. The dual lumen hemostatic valve device 100 can be used for delivering a guide catheter used in a coronary intervention procedure that concurrently or simultaneously uses more than one guide wire, such as in a bifurcation percutaneous coronary intervention (PCI) procedure.

In FIG. 1, the dual lumen hemostatic valve device 100 can include a distal Tuohy Borst or other exit port 102 providing an exit lumen 104. The exit lumen 104 can extend proximately into a manifold 106, where it can split into multiple lumens extending proximately from the manifold 106, such as into: (1) a first entry lumen 108 extending proximally from the manifold 106 via a first tube 110 to a first Tuohy Borst or other entry port 112; (2) a second entry lumen 114 extending proximally from the manifold 106 via a second tube 116 to a second Tuohy Borst or other entry port 118;

and (3) a third entry lumen 120 extending proximally from the manifold 106 via a third tube 122 to a third Tuohy Borst or other entry port 124.

The first tube 110, the second tube 116, and the third tube 122 can exit the manifold at divergent angles, such as in a Y-arrangement (or a W-arrangement, e.g., for more than two tubes) or the like. However, the first entry port 112 and the second entry port 118 can each include a proximal end portion oriented to be axially aligned to be parallel to each other. In this way, any guidewires (or other instruments) respectively extending proximally out from the first entry port 112 and the second entry port 118 can be aligned in parallel to each other. This parallel proximal end arrangement can help ease management of such guide wires or other instruments within the sterile field during the procedure. This can be compared to an approach using a first entry port 112 that diverges with respect to the second entry port 118, which causes diverging guidewires and makes wire management more difficult, particularly within the sterile field in the operating room. A balloon catheter or other stent delivery device can be inserted into the entry port 124 and can exit from the port 102, and can make use of one of the guidewires inserted into the first entry port 112 or the second entry port 112 for guiding the balloon catheter or other stent delivery device to its desired target location within the patient's body.

Each of the entry ports 112 and 118 can include a separate hemostatic valve 126, 128 that works independent of each other, such as to grip a corresponding guide wire and to provide a seal to inhibit bleed-back. The hemostatic valves 126, 128 can respectively include a spring-biased pushable plunger valve, which is easier and more convenient for a physician or other user to use than a threaded screw-in type valve. Each of the hemostatic valves 126, 128 can be independently actuated, such as via a lateral or other externally accessible button that is capable of being slid between two positions within a lateral slot, to respectively open and close a respective one of the hemostatic valves 126, 128. Within each of the hemostatic valves 126, 128, a plunger valve can include a tubular or other elongate member that, when actuated to open the valve, pushes through a tricuspid, bicuspid, or other similar opening on a seal membrane, which is otherwise normally closed in the absence of the elongate member having been actuated and thereby pushed through the opening in the seal membrane to open the seal.

The distal exit port 102 can include a partial-turn or other rotatable engagement feature 130 such as to permit rotatable twist on/off connection to a stent-delivery guide catheter or other instrument at the distal exit port 102.

Figure 2:
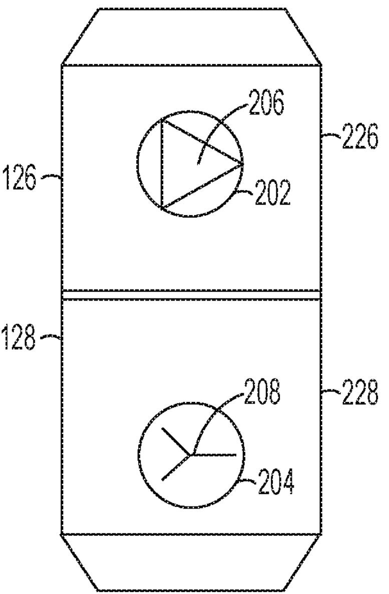
FIG. 2 shows an example of portions of separate and independently actuated hemostatic valves, including respective seal membranes providing respective seal openings.

FIG. 2 shows an example of portions of the separate and independently actuated hemostatic valves 126, 128, including respective seal membranes 202 and 204 providing respective seal openings 206, 208. In FIG. 2, the seal opening 208 is shown as a closed tricuspid valve in the seal membrane 204, and the seal opening 206 is shown as an open tricuspid valve in the seal membrane 202. By pushing its actuation button 226 from a more proximal to a more distal position, the hemostatic valve 126 is opened by depressing its corresponding spring-loaded plunger to push its elongate member through the opening 206. By returning its actuation button 226 from the more distal position to the more proximal position, the hemostatic valve 126 is closed. Similarly, by pushing its actuation button 228 from a more proximal to a more distal position, the hemostatic valve 128 is opened by depressing its corresponding spring-loaded plunger to push its elongate member through the opening 208. By returning its actuation button 228 from the more distal position to the more proximal position, the hemostatic valve 128 is closed.

To recap, the hemostatic valve device 100 can provide better management of multiple wires and coronary or other interventional devices during their concurrent or simultaneous use in complex coronary or other medical intervention procedure, thereby simplifying the procedure. It decreases challenges of entanglement and of accidental withdrawal of the guide wire or other instrument from its target location in a coronary vessel or elsewhere, thereby decreasing the chance of patient complications. This can be useful, particularly in a bifurcation percutaneous coronary intervention (PCI).

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A multiple lumen hemostatic valve device for use with a guide catheter in a medical intervention procedure, the valve device comprising:
- a manifold;
- a distal exit port, coupled to the manifold and providing an exit lumen;
- a first entry port, coupled to the manifold and providing a first entry lumen in communication with the exit lumen;
- a second entry port, coupled to the manifold and providing a second entry lumen in communication with the exit lumen; and
- wherein the first and second entry ports are arranged to be parallel to each other and respectively include independently operable first and second plunger valves.

2. The valve device of claim 1, further comprising a third entry port, coupled to the manifold and providing a third entry lumen in communication with the exit lumen.

3. The valve device of claim 2, in combination with a balloon stent delivery catheter insertable via the third entry lumen.

4. The valve device of claim 1, wherein the first and second plunger valves are biased.

5. The valve device of claim 1, wherein the first and second plunger valves are adapted to secure a guidewire, when closed, while sealing against bleed back through the corresponding one of the first and second plunger valves.

6. The valve device of claim 1, in combination with a first guidewire insertable via the first plunger valve and a second guidewire insertable via the second plunger valve.

7. The valve device of claim 1, in combination with a first intravascular instrument insertable via the first plunger valve and a second intravascular instrument insertable via the second plunger valve.

8. The valve device of claim 7, wherein the first intravascular instrument includes a guidewire.

9. The valve device of claim 8, wherein the second intravascular instrument includes a catheter.

10. The valve device of claim 1, comprising:
- a first tube, providing the first entry lumen, the first tube coupled to the manifold and the first entry port; and
- a second tube, providing the second entry lumen, the second tube coupled to the manifold and the second entry port.

11. The valve device of claim 10, further comprising:
- a third entry port, coupled to the manifold and providing a third entry lumen in communication with the exit lumen; and
- a third tube, providing the third entry lumen.

12. The valve device of claim 11, wherein the first, second, and third tubes define respective longitudinal axes respectively arranged at acute angles with respect to one another to diverge from the manifold.

13. The valve device of claim 12, wherein the first and second tubes respectively include bends to orient the first and second entry ports to be parallel to each other.

14. The valve device of claim 1, wherein the first and second plunger valves respectively include corresponding tricuspid valves.

15. The valve device of claim 1, wherein the distal exit port includes a partial-turn or other rotatable engagement feature to permit rotatable twist-on and twist-off connection to a stent-delivery guide catheter or other instrument at the distal exit port.

16. The valve device of claim 1, wherein the first and second plunger valves are spring-loaded.

* * * * *